United States Patent [19]

McGill

[11] 4,199,954
[45] Apr. 29, 1980

[54] METHOD OF STORING PHYSIOLOGICAL MATERIAL

[75] Inventor: Manley McGill, Wheaton, Md.

[73] Assignee: American National Red Cross, Washington, D.C.

[21] Appl. No.: 932,200

[22] Filed: Aug. 9, 1978

[51] Int. Cl.² ............................................. F25D 25/00
[52] U.S. Cl. ............................................. 62/62; 62/78; 424/101; 435/2
[58] Field of Search ................. 62/62, 78; 195/1.8; 424/101

[56] References Cited

U.S. PATENT DOCUMENTS

| | | | |
|---|---|---|---|
| 3,703,438 | 11/1972 | Dovgalev et al. | 195/1.8 |
| 4,030,314 | 6/1977 | Strehler | 62/78 |
| 4,059,967 | 11/1977 | Rowe et al. | 62/78 |

*Primary Examiner*—Ronald C. Capossela
*Attorney, Agent, or Firm*—Holman & Stern

[57] ABSTRACT

Human cells or tissue in suspension or immersion in physiological solution are stored at a basic storage temperature of about 4° C., and periodically subjected to a higher temperature within the range of from 25°–37° C. for a period of time and at intervals sufficient to inhibit irreversible losses in function and viability of the cells or tissue. The method is particularly suitable for the storage of blood platelet concentrates in plasma to be subsequently used in transfusions, enabling prolonged storage periods with improved overall effectiveness of the transfused platelets.

5 Claims, No Drawings

METHOD OF STORING PHYSIOLOGICAL MATERIAL

BACKGROUND OF THE INVENTION

This invention relates to the liquid storage of physiological material and, more particularly, to an improved storage procedure involving temperature cycling of the stored material to more effectively preserve its function and viability.

The liquid storage of human cells or tissue for subsequent use in transfusions, transplanatations or the like, has conveniently been carried out by maintaining such cells or tissue in suspension or immersion in physiological solution at normal refrigerator temperature, i.e., at about 4° C. This is the procedure which most blood banks have typically employed for many years for storing red blood cell, white blood cell, and platelet concentrates in plasma. However, 4° C. storage has certain limitations which substantially hinder its effectiveness for storage periods beyond about twenty-four hours.

A tremendous increase in recent years in the use of platelet transfusions for the control of thrombocytopenic bleeding, has led to a number of recent studies designed to improve the efficiency of platelet collection and storage techniques. The results of these studies have indicated that in certain respects, 22° C. storage of platelets is preferably to 4° storage, particularly when the storage period is to be greater than about twenty-four hours. The primary disadvantage of the 4° C. storage technique is that after about twenty-four hours at this temperature, the in vivo survival time of the transfused platelets drops from the "normal" level of about seven to eight days to a level of only about two to three days. With the 22° C. storage technique, on the other hand, the in vivo survival times of the transfused platelets are maintained at "normal" levels for up to seventy-two hours of storage time. However, this improved platelet viability provided by the 22° C. storage technique in comparison with 4° C. storage, is offset by a loss in the aggregating and hemostatic functions of the platelets upon their transfusion. Thus, while platelets stored at 4° C. for up to seventy-two hours of storage retain their immediate hemostatic effectiveness upon transfusion, platelets stored at 22° C. for the same period of time exhibit a significantly delayed hemostatic effectiveness upon transfusion. In addition to this loss in function, there is an increased risk of bacterial contamination for those platelets stored at 22° C. Hence, particularly where the stored platelets are to be used primarily for achieving immediate hemostasis, rather than mere prophylaxis, 4° C. storage offers important benefits which are not available with the 22° C. storage technique. Moreover, neither of these storage techniques has been found to be very effective for storing platelets for storage periods longer than about seventy-two hours.

It has previously been demonstrated that the function and viability of human cells and tissue are significantly affected by the presence or absence in the cells or tissue of microtubules. Losses in function and viability are generally associated with losses in microtubules. In human platelets, microtubules are thought to be essential for maintenance or stabilization of cell shape, and are necessary for secretion. Loss of platelet microtubules has resulted in loss of spreading capabilities, inhibition of aggregation, and probably contributes to spontaneous aggregation seen in stirred suspensions of cold platelets. In other cells, microtubules are involved in a variety of important cellular functions, and the processes of microtubule disassembly and reassembly in these cells are known to reflect complex biochemical mechanisms.

It has also previously been demonstrated that microtubules are sensitive to cold temperatures, and that irreversible microtubule disassembly occurs in platelets maintained at 4° C. continuously for more than about twenty-four hours. In view of the correlation between loss of microtubules in cells and tissue, and losses in their function and viability, it therefore appears likely that inhibiting irreversible microtubule disassembly is an important factor in developing a more efficient procedure for the storage of cells and tissue.

SUMMARY OF THE INVENTION

It is, accordingly, a primary object of the present invention to provide an improved method for the liquid storage of physiological materials which more effectively preserves their function and viability in comparison with previously employed storage techniques.

Another object of the invention is to provide a method in accordance with the preceding object, which effectively inhibits irreversible disassembly of microtubules in the stored material.

A further object of the invention is to provide a method in accordance with the preceding objects, which enables the storage of blood platelets with all of the benefits provided by 4° C. storage techniques, but with improved function and substantially increased in vivo survival times after transfusion.

Still another object of the invention is to provide a method in accordance with the preceding objects, which enables prolonged periods of storage time.

The above and other objects are achieved in accordance with the present invention by means of a temperature cycling storage procedure whereby a physiological material comprising a suspension or immersion of human cells or tissue in physiological solution is maintained at a basic storage temperature of about 4° C., and periodically subjected to a higher temperature within the range of from 25° to 37° C. for a period of time and at intervals sufficient to inhibit irreversible losses in function and viability of the cells or tissue. Depending upon the particular higher temperature employed, the period of time at such higher temperature may suitably range from about fifteen minutes to one hour, and the intervals between such periods of time may suitably range from four to twenty-four hours. In this manner, the irreversible microtubule disassembly which would ordinarily occur with continuous 4° C. storage for more than about twenty-four hours, is inhibited, and correspondingly, the function and viability of the cells or tissue are more effectively preserved. The procedure enables storage of blood platelets with all of the benefits provided by continuous 4° C. storage, but with improved function, with substantially increased in vivo survival times after transfusion, approaching that achieved with 22° C. storage, and with effective storage time extended up to about ninety-six hours.

DESCRIPTION OF PREFERRED EMBODIMENTS

The temperature cycling method of the present invention may suitably be used for the liquid storage of a wide variety of human cells or tissue, including, for example, platelets, erythrocytes, granulocytes, lymphocytes, bone marrow tissue, and organs for transplantation. The method is particularly suitable for the storage of blood cellular element concentrates in plasma for subsequent use in transfusions. When utilized for the storage of blood platelet concentrates in plasma, the storage procedure of the present invention yields a transfusion product which is superior in overall effectiveness to that produced by either continuous 4° C. storage or 22° C. storage.

The storage procedure of the present invention is basically a 4° C. storage, but with periodic warming pulses to a higher temperature within the range of from 25° to 37° C. for a period of time and at intervals sufficient to inhibit the irreversible losses in function and viability of the cells or tissue which would otherwise occur with a continuous and uninterrupted 4° C. storage. The requisite period of time of each warming pulse varies inversely with the particular temperature employed for the warming pulse, ranging from a minimum from about fifteen minutes at 37° C. to a minimum to about one hour at 25° C. The intervals between each warming pulse should be of sufficiently long duration so that the procedure is still basically a 4° C. storage, but of sufficiently short duration so as to ensure interruption of the continuous 4° C. storage before irreversible losses in function and viability of the stored material can take place. In general, such intervals may vary from a minimum of about four hours to a maximum of about twenty-four hours. The warming pulses may be carried out by any suitable means, for example, by means of a water bath.

A storage protocol which has found to be particularly effective for the storage of blood platelet concentrates in plasma comprises periodically interrupting the 4° C. storage of the concentrate by subjecting it to a temperature of about 37° C. for periods of about thirty minutes duration and at intervals of about twelve hours.

Since the temperature cycling storage technique of the present invention is still basically a 4° C. storage procedure, it retains all of the benefits characteristic of uninterrupted continuous 4° C. storage. For example, in the case of platelet concentrates stored in accordance with the present technique, the stored platelets will not lose their immediate hemostatic effectiveness, and thus can be effectively utilized in transfusions following storage for achieving hemostasis. In addition, the present technique eliminates many of the negative features associated with uninterrupted continuous 4° C. storage, including the functional defects caused by irreversible microtubule disassembly, irreversible loss of the discoid, spindle shape of the platelets, and spontaneous aggregation of the platelets upon stirring. Furthermore, the drastic reduction in the in vivo survival time of the stored platelets subsequent to transfusion which is characteristic of the uninterrupted continuous 4° C. storage procedure, is not induced by the temperature cycling storage technique of the present invention. Platelets stored for seventy-two hours by means of the temperature cycling technique have been found to have an in vivo survival time subsequent to transfusion of from five to six days, in comparison with the "normal" value of from seven to eight days, and with the value of from two to three days exhibited by platelets stored for the same period continuously at 4° C. Moreover, while neither of the previously employed continuous 4° C. and continuous 22° C. platelet storage procedures is effective for storage periods beyond about seventy-two hours, in vitro test data indicate that the temperature cycling storage technique of the present invention may be utilized for extension of platelet storage to up to about ninety-six hours.

The invention is further illustrated by way of the following examples.

EXAMPLE 1

Blood platelet concentrates in plasma were prepared as follows. Normal human venous blood was collected from volunteer donors in triple blood packs (Fenwal Laboratories, Morton Groove, Ill.) containing citrate-phopsphate-dextrose as anticoagulant. The whole blood was centrifuged for 3.5 minutes at 2400 g and platelet-rich plasma was expressed into transfer packs. Platelets were concentrated into 60 ml of plasma by centrifugation of the platelet-rich plasma for ten minutes at 3000 g. The centrifuged platelet concentrates were stored undisturbed for one hour at 22° C. before final resuspension. Each platelet concentrate was then sealed in an individual plastic bag as a precaution against possible water bath contamination, and placed into a 4° C. refrigerator.

One group of the platelet concentrate units was subjected to the temperature cycling storage procedure in accordance with the present invention. The temperature cycling procedure was carried out by removing the platelet concentrate units from the refrigerator every twelve hours, immersing them in a 37° C. water bath for thirty minutes, and thereafter returning them to the 4° C. refrigerator.

The remaining group of platelet concentrate units was stored continuously in the 4° C. refrigerator to serve as a control.

EXAMPLE 2

Samples of both the temperature cycled and control stored platelet concentrates of Example 1 were subjected to electron microscopy after varying periods of storage time. Unless noted otherwise, all platelet concentrate samples for electron miscroscopy were incubated in a 37° C. water bath for fifteen minutes prior to their fixation in 37° C. glutaraldehyde, this being the minimum time required to bring platelet concentrate samples to 37° C. The platelets in the concentrate were fixed by the addition of equal volumes of 0.2% glutaraldehyde preheated to 37° C. Platelets in 0.2% glutaraldehyde were allowed to fix for one hour at room temperature before centrifugation and resuspension in 3–5 ml of 3% glutaraldehyde for one hour. All samples were post-fixed in osmium tetroxide, pre-stained in uranyl acetate, dehydrated with ethyl alcohol, and embedded in epoxy resin.

In order to quantitate the numbers of microtubules in random thin sections of platelets, a series of seven to ten micrographs (at 10,000×) were taken of non-contiguous sections of each platelet sample. Numbers of platelet sections and microtubules, in all planes of section, were counted in prints from each micrograph at a final magnification of 27,000×. Cytoplasmic extensions presumed to be platelet pseudopodia, but containing no organelles which would identify them as such, were not included in platelet section counts. The microtubule count of each platelet sample tested was determined as the number of microtubules counted divided by the number of platelet sections examined, and expressed as microtubules/section.

For purposes of comparison, the microtubule count of freshly collected platelet concentrates at 37° C. was determined as averaging 13.5. Also, one platelet concentrate control sample was tested after one hour at 4° C., but without the fifteen minute 37° C. water bath incubation, and found to have a microtubule count of less than 0.1.

The test results with the platelet concentrate control samples indicated that up to about twenty-four hours of continuous 4° C. storage, the fifteen minute 37° C. water bath incubation resulted in reassembly of microtubules to bring the microtubule count back up to at least within the range of 0.5–1.0. However, beyond twenty-four hours of continuous 4° C. storage, the fifteen minute 37° C. water bath incubation was ineffective for bringing the microtubule count back up above 0.1, indicating irreversible microtubule disassembly. After about forty-eight hours of continuous 4° C. storage, the microtubule count diminished to substantially zero.

With the temperature cycled platelet concentrate samples, the test results were quite different. The fifteen minute 37° C. water bath incubation, even after forty-eight hours of storage, results in reassembly of microtubules to bring the microtubule count back up to within the range of 0.5–1.0. Specifically, the microtubule count was 0.9 after fifty-six hours of storage, 0.8 after sixty-four hours storage, and 0.5 after seventy-two hours storage.

The electron micrographs further showed that after fifty-six hours of continuous 4° C. storage, the platelets in the control samples exhibited a loss of their discoid, spindle shape, as well as spontaneous aggregation upon stirring. On the other hand, the platelets in the temperature cycled samples, after seventy-two hours storage, had retained their discoid, spindle shape, and exhibited no spontaneous aggregation upon stirring.

EXAMPLE 3

In order to quantitatively determine the extents of spontaneous aggregation and initial shape change response indicated qualitatively by the electron micrographs as described above in Example 2, freshly collected platelet concentrates and both the temperature cycled and control stored platelet concentrates of Example 1, were subjected to platelet aggregometry on a Payton aggreometer (Payton Associates, Inc., Buffalo, N.Y.). Platelet samples consisting of 0.1 ml platelet concentrate and 0.4 ml platelet-poor plasma were placed in aggregometer cuvettes, incubated for fifteen minutes in a 37° C. water bath, and then placed in aggregometer wells also at 37° C. Base lines for 0 and 100% light transmission were set with platelet-rich plasms and platelet-poor plasma, respectively. Stir bars were added to the cuvettes, and the effect of stirring on the platelet samples was observed for three minutes. An increase in percent light transmission during this three minute period, as indicated by downward movement of the recorder pen, denotes spontaneous aggregation. Thereafter, 40 μm ADP (adenosine-5'-diphosphate) was added to the platelet sample, and aggregation of the platelets was observed as increases in percent light transmission, as indicated by erratic, downward movements of the recorder pen. An initial shape change response of the platelets immediately after addition of the ADP was observed as a transient decrease in percent light transmission, as indicated by an upward movement of the recorder pen, prior to the ADP-induced aggregation.

A quantitation, in light transmission units, was made of the spontaneous aggregation and the initial shape change response of freshly collected platelet concentrates and both the temperature cycled and control stored platelet concentrates of Example 1, at twenty-four, forty-eight and seventy-two hours of storage. The test results are set forth in Table I, below, wherein the storage period of "0" represents the freshly collected platelet concentrates.

TABLE I

| Storage Period, Hrs. | 0 | 24 | 48 | 72 |
| --- | --- | --- | --- | --- |
| Spontaneous Aggregation, light transmission units | | | | |
| (A) Temperature cycled samples | 0.0 | 0.0 | 0.0 | 0.0 |
| (B) Control samples | 0.0 | 0.7 | 1.7 | 2.2 |
| Initial Shape Change Response, light transmission units | | | | |
| (A) Temperature cycled samples | 4.6 | 2.0 | 1.5 | 1.4 |
| (B) Control samples | 4.7 | 0.5 | 0.2 | 0.06 |

The test data set forth in Table I show that continuous 4° C. storage results in spontaneous aggregation of the platelets upon stirring, beginning after about twenty-four hours of storage and becoming much more pronounced after forty-eight to seventy-two hours of storage. It should be noted that an increase of 2.0 light transmission units during spontaneous aggregation was equivalent to 10–15% of the total increase in light transmission units after the maximum aggregation induced by the ADP. In addition, the platelets stored continuously at 4° C. exhibited a large and rapid loss in initial shape change response to ADP after only twenty-four hours of storage, indicating a loss of their discoid, spindle shape. Conversely, the temperature cycled platelets did not show the aggregation abnormalities observed in platelets stored continuously at 4° C. Throughout seventy-two hours of storage, the temperature cycled platelets showed no spontaneous aggregation upon stirring, and furthermore exhibited a substantial initial shape change response to ADP, indicating retention of their discoid, spindle shape. It should be noted that the initial shape change response exhibited by the temperature cycled platelet samples after seventy-two hours of storage was over twenty-times greater than that exhibited by the control samples after the same period of storage, and about three times greater than that exhibited by the control samples after only twenty-four hours of storage. It should also be noted that a single 37° C. warming pulse after forty-eight to seventy-two hours of continuous 4° C. storage had no effect on the above-described test values obtained with continuous 4° C. storage.

EXAMPLE 4

Platelet recovery from hypotonic shock was measured on samples of freshly collected platelet concentrates and of both the temperature cycled and control stored platelet concentrates of Example 1, after storage periods of twenty-four, forty-eight, seventy-two and ninety-six hours. The procedure employed for measuring recoveries from hypotonic shock was designed after methods described by Valeri et al (Transfusion, 14:331, 1974) and Kim et al (Transfusion, 14:130, 1974). Using a Cary Model 118 spectrophotometer (Varian, Palo Alto, Calif.) set to measure absorbance at 610 nm, reference and test light beams were balanced at zero optical density with cuvettes containing 0.6 ml of platelet-poor plasma and 0.3 ml of saline. Test cuvettes were removed and refilled with 0.6 ml of platelet concentrate and 0.3 ml of saline. A range of 0–0.5 absorbance units was used for the recorder chart full-scale and various amounts of absorbance suppression were used to allow optical density changes to occur within the 0–0.5 range. After balance and range adjustments were established, the optical density of platelet-rich plasma plus saline was recorded. Test cuvettes were then refilled with 0.6 ml of the platelet concentrate sample to be tested followed by addition of 0.3 ml distilled water, mixed by inversion, and immediately placed back into test cuvette holders. Rapid losses in optical density followed by recoveries in optical density were recorded for ten minutes. Increases in optical density units during the first two minutes of recovery were the values used to assess recovery. Fresh platelet values from each donor unit were arbitrarily set at 100% recovery, and stored platelet recoveries from the same units were expressed as percents of fresh sample values. The temperature of all reagents and cuvette holders was maintained at 22° C.

The test results are set forth in Table II, below, wherein the test values given for the ninety-six hour storage period represent the mean ±1 standard deviation of three separate test samples, and all other test values represent the mean ±1 standard deviation of seven different test samples. It should also be noted that the comparisons between the temperature cycled samples and the control samples were performed on split units of platelet concentrates obtained from the same donors.

TABLE II

| Storage Period, hrs. | 24 | 48 | 72 | 96 |
|---|---|---|---|---|
| % Recovery from Hypotonic shock | | | | |
| (A) Temperature cycled samples | 70 ± 11 | 62 ± 5 | 56 ± 10 | 50 ± 10 |
| (B) Control samples | 56 ± 14 | 43 ± 16 | 36 ± 7.5 | 30 ± 2.5 |

The test data set forth in Table II clearly show that temperature cycled platelet concentrates exhibit a significantly improved recovery from hypotonic shock in comparison with platelet concentrates stored continuously at 4° C. It is particularly significant to note that the temperature cycled platelet concentrates had recovery values after ninety-six hours of storage equal to the values exhibited by the platelet concentrates stored continuously at 4° C. for twenty-four to forty-eight hours. Since recovery from hypotonic shock is employed as an in vitro measure of in vivo survival, the above data indicate that the temperature cycling storage procedure of the present invention may be used to extend blood bank storage of platelets to ninety-six hours.

What is claimed is:

1. In the method of storing a physiological material comprising a suspension or immersion of human cells or tissue in physiological solution at a basic storage temperature of about 4° C., the improvement consisting of a temperature cycling procedure which comprises periodically interrupting the 4° C. storage by subjecting said material to a higher temperature within the range of from 25° to 37° C. for a period of time and at intervals sufficient to inhibit the irreversible losses in function and viability of said cells or tissue which would otherwise occur with a continuous and uninterrupted 4° C. storage.

2. The method of claim 1, wherein said period of time is within the range of from fifteen minutes to one hour, and said intervals are within the range of from four to twenty-four hours.

3. The method of claim 2, wherein said material is a blood cellular element concentrate in plasma.

4. The method of claim 3, wherein said material is a blood platelet concentrate in plasma.

5. The method of claim 4, wherein said blood platelet concentrate is periodically subjected to a temperature of about 37° C. for periods of about thirty minutes duration and at intervals of about twelve hours.

* * * * *